United States Patent
Bang-Andersen et al.

(10) Patent No.: US 6,200,999 B1
(45) Date of Patent: Mar. 13, 2001

(54) 3-ALKOXYISOXAZOL-4-YL-SUBSTITUTED 2-AMINO CARBOXYLIC ACID COMPOUNDS

(75) Inventors: Benny Bang-Andersen, Copenhagen; Klaus Peter Bøgesø, Hørsholm; Povl Krogsgaard-Larsen, Allerød; Sibylle Moltzen Lenz, Gentofte, all of (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/269,356

(22) PCT Filed: Oct. 3, 1997

(86) PCT No.: PCT/DK97/00426

§ 371 Date: May 20, 1999

§ 102(e) Date: May 20, 1999

(87) PCT Pub. No.: WO98/15542

PCT Pub. Date: Apr. 16, 1998

(30) Foreign Application Priority Data

Oct. 4, 1996 (DK) .................................................. 1092/96

(51) Int. Cl.[7] .......................... A61K 31/42; A61K 31/425; C07D 261/10; C07D 261/12; C07D 261/18

(52) U.S. Cl. ............................ 514/380; 514/372; 548/213; 548/243

(58) Field of Search .............................. 548/243; 514/380

(56) References Cited

FOREIGN PATENT DOCUMENTS

| 0 456 519 A1 | 11/1991 | (EP) | .............................. C07D/413/12 |
|---|---|---|---|
| WO 9410145 A1 | 5/1994 | (WO) | ........................... C07D/211/32 |
| 95/12587 * | 5/1995 | (WO) . | |

OTHER PUBLICATIONS

Benny Bang–Andersen, et al.; "Heteroaryl Analogues of AMPA, Synthesis and Quantitative Structure—Activity Relationships"; *J. Medicinal Chemistry*, vol. 40, No. 18; pp. 2831–2842 (Aug. 29, 1997).

Ulf Madsen, et al; "Synthesis and Pharmacology of Highly Selective Carboxy and Phosphono Isoxazole Amino Acid AMPA Receptor Antagonists", *J. Medicinal Chemistry*, vol. 39, No. 8, pp. 1682–1691 (Apr. 1996).

Shaun D. Abbott, et al.; "Synthesis and Testing of Heterocyclic Analogues of Diaminopimelic Acid (DAP) as Inhibitors of DAP Dehydrogenase and DAP Epimerase"; *J. American Chemical Society;* vol. 116, No. 15; pp. 6513–6520 (1994).

U. Madsen, et al.; "Excitatory Amino Acid Receptor Antagonists: Synthesis and Pharamacology of 3–(Carboxymethoxy) Isoxazoles Derived from AMPA"; Abstract, *Bioorganic & Medicinal Chemistry Letters*, vol. 3, No. 8, pp. 1649–1654 (1993).

Jorn Lauridsen et al., "Ibotenic Acid Analogues. Synthesis Molecular Flexibility, and in Vitro Activity of Agonists and Antagonists at Central Glutamic Acid Receptors," *J. Med. Chem*, vol. 28, pp. 668–672 (1985).

Inge T. Christensen et al., "Excitatory Amino Acid Agonists and Partial Agonists," *Drug Design and Delivery*, vol. 5, pp. 57–71 (1989).

Jan J. Hansen et al., "Structural, Conformational, and Stereochemical Requirements of Central Excitatory Amino Acid Receptors," *Medicinal Research Reviews*, vol. 10, No. 1, pp. 55–94 (1990).

* cited by examiner

Primary Examiner—Laura L. Stockton
(74) Attorney, Agent, or Firm—Darby & Darby

(57) ABSTRACT

(3-Alkoxyisoxazol-4-yl)-substituted 2-amino carboxylic acid derivatives and sulfur analogues thereof having general formula (I) or (II),

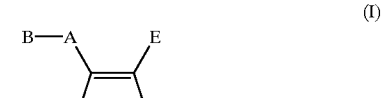

(I)

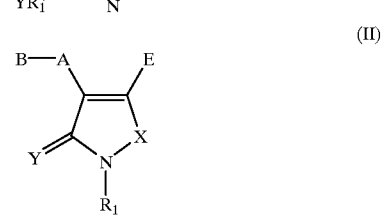

(II)

wherein $R_1$ is hydrogen, alkyl, alkenyl, alkynyl, cycloalk(en)yl, cycloalk(en)yl-alk(en/yn)yl or optionally substituted phenyl-alk(en/yn)yl; A is a bond or a hydrocarbon spacer group; B is a group $—CR_a(NR_bR_c)—COOR_5$ wherein $R_a$–$R_c$ are independently hydrogen or alkyl, and $R_5$ is defined as $R_1$ or pivaloyloxymethyl, or B is a group of Formula (III),

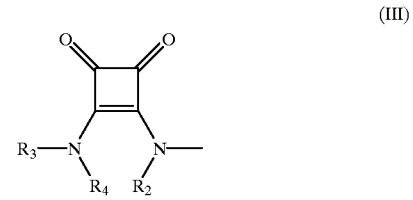

(III)

wherein $R_2$, $R_3$ and $R_4$ are independently selected from hydrogen, a non-aromatic hydrocarbon group, phenyl- and thienyl-alkyl, and a hetero aliphatic group, or $R_3$ and $R_4$ are connected, thereby forming an alkylene, alkenylene or alkynylene group, or $R_4$ and $R_2$ are connected in order to form an alkylene, alkenylene or alkynylene group, optionally substituted with hydroxy or methyl, or to form $CH_2—O—CH_2$; E is $COOR_6$, where $R_6$ is defined as $R_5$, or E is a tetrazolyl or triazolyl; X is O or S; and Y is O or S; are excitatory amino acid (EAA), in particular AMPA and/or NMDA receptor ligands, useful in the treatment of cerebral ischaemia, Huntington's disease, epileptic disorders, Parkinson's disease, Alzheimer's disease, schizophrenia, pain, depression and anxiety.

23 Claims, No Drawings

3-ALKOXYISOXAZOL-4-YL-SUBSTITUTED 2-AMINO CARBOXYLIC ACID COMPOUNDS

This application is a 371 of PCT/DK97/00426 filed Oct. 3, 1997.

FIELD OF THE INVENTION

The present invention relates to a novel class of (3-alkoxyisoxazol-4-yl)-substituted 2-amino carboxylic acid derivatives and sulfur analogues thereof. The compounds are excitatory amino acid (EAA) receptor ligands, in particular AMPA and/or NMDA receptor ligands useful in the treatment of cerebral ischaemia, Huntington's disease, epileptic disorders, Parkinson's disease, Alzheimer's disease, schizophrenia, pain, depression and anxiety.

BACKGROUND OF THE INVENTION

As a result of extensive studies of excitatory mechanisms in the central nervous system (CNS) during the past three decades, there is now a consensus of opinion that (S)-glutamate (Glu) is the major EAA neurotransmitter in the CNS (Lodge, D. *Excitatory Amino Acids in Health and Disease.* J. Wiley & Sons: Chichester, 1988; Wheal, H.; Thomson, A. *Excitatory Amino Acids and Synaptic Transmission.* Academic Press: London, 1991; Meldrum, B. S. *Excitatory Amino Acid Antagonists.* Blackwell Sci. Publ.: Oxford, 1991; Krogsgaard-Larsen, P.; Hansen, J. J. *Excitatory Amino Acid Receptors: Design of Agonist and Antagonists.* E. Horwood: Chichester, 1992). Glu-operated neurotransmission is mediated by a large number of receptors, classified into at least four heterogeneous families of receptors named NMDA, AMPA, kainic acid, and metabotropic classes of receptors (Monaghan, D. T., et al. *Ann. Rev. Pharmacol. Toxicol.* 1989,29, 365–402; Watkins, J. C.; Krogsgaard-Larsen, P.; Honoré, T. *Trends Pharmacol. Sci.* 1990,11, 25–33; Simon, R. P. *Excitatory Amino Acids. Thieme Med. Publ.:* New York, 1992).

There is very strong evidence supporting the view that excessive excitation mediated by EAA receptors ("excitotoxicity") is a factor of major importance in cerebral ischaemia following stroke, head injury, asphyxia, subarachnoid haemorrhage, cardiac arrest and other situations (Lodge, D., 1988 supra; Meldrum, B. S., 1991 supra). It has been shown in animal models that the damages caused by various ischaemic conditions can be inhibited by the administration of Glu-antagonists. So, although the relative importance of the different classes of EAA receptors in the phenomena underlying ischaemic insults is unclear, it is generally agreed that EAA receptor antagonists are potential therapeutic agents in these conditions.

Accumulating evidence derived from different lines of neurochemical and pharmacological research suggests that derailed EAA receptor mechanisms, possibly including "excitotoxicity", play a role in Huntington's disease (Young, A. B.; et al. *Science* 1988,241, 981–983), epileptic disorders (Krogsgaard-Larsen, P.; Hansen, J. J., 1992 supra), Parkinson's disease (Klockgether, T.; Turski, L. *Trends. Neurosci.* 1989,12, 285–286), and Alzheimer's disease (Greenamyre, J. T.; Maragos, W. F. *Cerebrovasc. Brain. Metab. Rev.* 1993,5, 61–94; Francis, P. T., et al. *J. Neurochem.* 1993,60, 1589–1604).

Furthermore, central EAA receptors may be involved in the synaptic mechanisms underlying schizophrenia (Reynolds, G. P. *Trends. Pharmacol. Sci.* 1992,13, 116–121), pain and anxiety (Drejer, J. In: *Excitatory Amino Acid Receptors: Design of Agonists and Antagonists* (Eds. Krogsgaard-Larsen, P.; Hansen, J. J.) E. Horwood: Chichester 1992, pp. 352–375) and depression (Trullas, R., Skolnick, P., *Eur. J. Pharmacol.* 1990, 185, 1–10 and Trullas et al., *Eur. J. Pharmacol.* 1991, 203, 379–385. So, reduced function of EAA receptors (EAA hypoactivity) seems to play a role in, for example, schizophrenia (Deutsch, S. I.; et al. *Clin. Neuropharmacol.* 1989,12, 1–13) and some of the clinical symptoms seen in Alzheimer's disease (Greenamyre, J. T.; et al. *Prog. Neuro-Psychopharmacol. & Biol. Psychiat.* 1988,12, 421–430). It is possible that "excitotoxicity" as well as EAA hypoactivity are involved in the complex mechanisms associated with Alzheimer's disease (Greenamyre, J. T.; 1988 supra; Greenamyre, J. T.; Maragos, W. F., 1993, supra).

Accordingly, EEA receptor ligands are considered to be useful in the treatment of cerebral ischaemia, Huntington's disease, epileptic disorders, Parkinson's disease, Alzheimer's disease, anxiety, schizophrenia, depression and pain.

Most EAA receptor agonists so far tested, show more or less pronounced neurotoxicity in model systems and consequently clinical uses of such compounds may be limited (Carlsson, M.; Carlsson, A. *Trends. Neurosci.* 1990,13, 272–276) (Willetts, J.; Balster, R. L.; Leander, J. D. *Trends. Pharmacol. Sci.* 1990,11,423–428).

Partial EAA agonists showing appropriate balance between agonism and antagonism may, on the other hand, have considerable therapeutic interest, cf. the above indications, (Greenamyre, J. T.; 1988 supra; Christensen, I. T.; et al. *Drug. Des. Del.* 1989,5, 57–71; Francis, P. T.; et al. *J. Neurochem.* 1993,60, 1589–1604). Partial agonists may, by virtue of their EAA antagonist profile, show therapeutically useful neuroprotection and, at the same time, be sufficiently agonistic to prevent total blockade of the neurotransmission mediated by the particular EAA receptor.

ATPA, the 5-tert-butyl analogue of AMPA ((RS)-2-amino-3-(3-hydroxy-5-methylisoxazol-4-yl)propionic acid), has been disclosed to be systemically active whereas it has not been reported to show neurotoxic effects in animals (Ornstein, P. L.; et al. *J. Med. Chem.* 1993,36, 2046–2048; Lauridsen, J.; Honoré, T.; Krogsgaard-Larsen, P. *J.Med.Chem.* 1985, 28, 668–672).

Like AMPA itself, a number of mono- and bicyclic AMPA analogues have been found to show selective agonist effects at AMPA receptors (Hansen, J. J.; Krogsgaard-Larsen,P. *Med. Res. Rev.* 1990,10, 55–94; Krogsgaard-Larsen, P.; Hansen, J. J., 1992 supra;). One of these analogues, (RS)-2-Amino-3-(3-hydroxy-5-phenylisoxazol-4-yl)propionic acid (APPA), in which the methyl group of AMPA has been replaced by a phenyl group, shows a weak but unique partial agonist profile (Christensen, I. T.; et al., 1989, supra).

ACPA ((RS)-2-amino-3-(3-carboxyoxy-5-methylisoxazol-4-yl)propionic acid) has been described as a potent AMPA receptor agonist (Madsen, U. and Wong, E. *J. Med. Chem.* 1992,35, 107–111).

Furthermore, WO-A1 95012587 discloses a class of (5-arylisoxazol-4-yl)- or (5-arylisothiazol-4-yl)-substituted 2-amino carboxylic acid compounds as EAA-receptor ligands.

As seen from the above non-neurotoxic, CNS-active EEA receptor ligands with good penetration into the CNS are highly desirable for treating the various diseases mentioned and, accordingly, it is the object of the present invention to provide such new drugs.

SUMMARY OF THE INVENTION

It has now been found that a novel class of (3-alkoxyisoxazol-4-yl)-substituted 2-amino carboxylic acid derivatives and sulfur analogues thereof are EAA receptor ligands, in particular AMPA and/or NMDA receptor ligands.

Accordingly, the present invention relates to a novel class of compounds having general Formula I or II

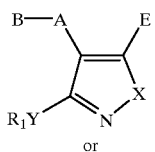

I or

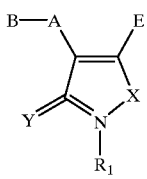

II wherein $R_1$ is hydrogen, $C_{1-6}$ alkyl, $C_{2-6}$ alkenyl, $C_{2-6}$ alkynyl, cycloalk(en)yl, cycloalk(en)yl-$C_{1-6}$ alk(en/yn)yl or phenyl-$C_{1-6}$ alk(en/yn)yl the phenyl group being optionally substituted with $CF_3$, halogen, $C_{1-6}$ alkyl or $C_{1-6}$ alkoxy;

A is a bond or a spacer group selected from $C_{1-6}$ alkylene, $C_{2-6}$ alkenylene or $C_{2-6}$ alkynylene, and cycloalkylene;

B is a group —$CR_a(NR_bR_c)$—$COOR_5$ wherein $R_a$-$R_c$ are independently hydrogen or $C_{1-6}$ alkyl, and $R_5$ is defined as $R_1$ or pivaloyloxymethyl, or B is a group of Formula III

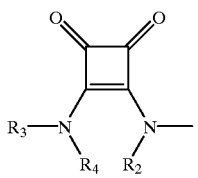

III wherein $R_2$, $R_3$ and $R_4$ are independently selected from the group consisting of
a) hydrogen, $C_{1-6}$ alkyl, $C_{2-6}$ alkenyl, $C_{2-6}$ alkynyl, cycloalk(en)yl, cycloalk(en)yl-$C_{1-6}$ alk(en/yn)yl, phenyl-$C_{1-6}$ alkyl, thienyl-$C_{1-6}$-alkyl, and
b) $C_{1-6}$ alkyl, $C_{2-6}$ alkenyl and $C_{2-6}$ alkynyl in which one or more carbon atoms are replaced by N, O, and/or S; or $R_3$ and $R_4$ are connected thereby forming a $C_2$-$C_6$ alkylene, $C_2$-$C_6$ alkenylene or $C_2$-$C_6$ alkynylene group; or $R_4$ and $R_2$ are connected in order to form a $C_1$-$C_3$ alkylene, $C_2$-$C_3$ alkenylene or $C_2$-$C_3$ alkynylene group optionally mono- or di-substituted with hydroxy or methyl, or to form $CH_2$—O—$CH_2$;

E is $COOR_6$, where $R_6$ is defined as $R_5$, or E is tetrazol-5-yl, 1,2,4-triazol-3-yl or 1,2,3-triazol-4-yl X is O or S; Y is O or S; and pharmaceutically acceptable salts thereof.

In another aspect, the invention relates to a method for the preparation of the novel compounds of Formula I or II.

In yet another aspect, the invention relates to a pharmaceutical composition comprising a novel compound of Formula I or II together with a suitable pharmaceutically acceptable carrier or diluent.

In yet another aspect, the invention relates to the use of a compound of Formula I or II for preparing a pharmaceutical composition for treatment of cerebral ischaemia, Huntington's disease, epileptic disorders, Parkinson's disease, Alzheimer's disease, schizophrenia, pain, depression or anxiety.

Some compounds of the invention have been found to be AMPA receptor ligands with affinities in micromolar concentrations and some compounds have been found to bind to NMDA receptors. Furthermore, some of the compounds of the invention were found to be agonists whereas others were found to be antagonists. Thus the compounds of the invention are useful in the treatment of cerebral ischaemia, Huntington's disease, epileptic disorders, Parkinson's disease, Alzheimer's disease, schizophrenia, pain, depression and anxiety. The compounds wherein $R_5$ and/or $R_6$ are not hydrogen are prodrugs for the corresponding compounds wherein $R_5$ and $R_6$ are hydrogen.

DETAILED DESCRIPTION OF THE INVENTION

Some of the compounds of general Formula I or II may exist as optical isomers thereof, and such optical isomers are also embraced by the invention.

In general Formula I and II, the term $C_{1-6}$ alkyl is intended to mean a straight chain or branched alkyl group having from 1 to 6 C atoms, inclusive, such as methyl, ethyl, 1-propyl, 2-propyl, 1-butyl, 2-butyl, 2-methyl-2-propyl etc. Similarly, $C_{2-6}$ alkenyl and $C_{2-6}$ alkynyl designate such straight chain or branched groups having 2 to 6 C-atoms and $C_{1-6}$ alkylene, $C_{2-6}$ alkenylene and $C_{2-6}$ alkynylene designate such branched or straight chain divalent groups. Cycloalkyl designates such a group having 3–7 carbon atoms and the term $C_{1-6}$-alkoxy designates such groups having a $C_{1-6}$ alkyl, $C_{2-6}$ alkenyl or $C_{2-6}$ alkynyl moiety as defined above.

The term "alk(en/yn)yl" means that the group may be an alkyl, alkenyl or alkynyl group.

The term bond (defined for A) means that B may be attached directly to the 4-position of the isoxazole ring.

Halogen means fluoro, chloro, bromo or iodo.

Some of the compounds of the general Formula I or II may exist as pharmaceutically acceptable salts thereof which are also embraced by the invention.

The salts of the compounds of the general Formula I or II are salts formed with non-toxic organic acids, e.g. maleic, fumaric, benzoic, ascorbic, oxalic, tartaric, lactic and malic acid, or inorganic acids, e.g. hydrochloric, hydrobromic, sulfuric, phosphoric and nitric acid or they may be salts of inorganic bases such as alkali metal salts, e.g. sodium, potassium, or lithium salts, alkaline earth metal salts, e.g. calcium or magnesium salts, or ammonium salts or salts of organic bases.

In Formula I and II, A is preferably a bond or $C_1C_3$ alkylene, most preferably methylene.

B is preferably —$CR_a(NR_bR_c)$—$COOR_5$ wherein $R_b$-$R_c$ are hydrogen and $R_a$ is hydrogen or $C_{1-6}$ alkyl, conveniently methyl, or a group of Formula III wherein $R_2$, $R_3$ and $R_4$ are hydrogen or $C_{1-6}$ alkyl, or $R_4$ and $R_2$ are connected in order to form a $C_1$-$C_3$ alkylene group. Most preferably, B is —$CH(NH_2)$—COOH or a group of Formula III wherein each of $R_2$, $R_3$ and $R_4$ are hydrogen.

Preferably, E is COOH, triazolyl or tetrazolyl, preferably COOH. Another subgroup comprises the compounds wherein E is $COOR_6$ where $R_6$ is not H. According to a preferred subgroup of the compounds of the invention X and Y are O. Other subgroups are those wherein X is O and Y is S; Y is O and X is S; and X and Y are S, respectively.

$R_1$ is preferably $C_{1-6}$ alkyl, $C_{2-6}$ alkenyl or $C_{2-6}$ alkynyl. Particularly suitable $R_1$ groups are methyl, ethyl, propyl, butyl and propargyl.

In a preferred embodiment of the invention the compound is a compound of Formula I wherein A is a bond or $C_1$–$C_3$ alkylene, B is —CH(NH$_2$)—COOH or a group of Formula III wherein each of $R_3$, $R_4$ and $R_2$ are hydrogen, X and Y are both oxygen, and $R_1$ is $C_{1-6}$ alkyl, $C_{2-6}$ alkenyl or $C_{2-6}$ alkynyl. Particularly suitable $R_1$ groups are methyl, ethyl, propyl, butyl and propargyl.

According to the invention, the compounds of Formula I or II are prepared by the following methods. For the sake of simplicity the reactions a)–e) and g)–h) are only shown for Formula I. Same methods may be used with respect to Formula II.

a) in order to obtain a compound of Formula I wherein B is a —CR$_a$(NR$_b$R$_c$)—COOR$_5$ wherein R$_a$–R$_c$ and R$_5$ are as previously defined, and at least one of R$_b$, R$_5$ and R$_6$ is hydrogen, deprotection of a compound of the general Formula IV

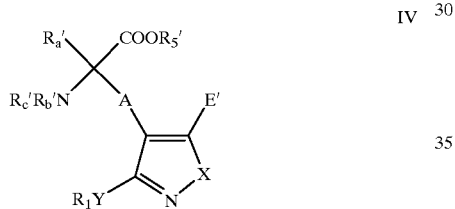

IV wherein $R_1$, A, X and Y are as previously defined, $R_a'$–$R_c'$, E' and $R_5'$ are defined for $R_a$–$R_c$, and E and $R_5$, respectively, or they are protection groups, provided that at least one of E', $R_5'$ and $R_c'$ is a protection group;

b) in order to obtain a compound of Formula I wherein B is a —CR$_a$(NR$_b$R$_c$)—COOR$_5$ group wherein R$_b$, R$_c$ and R$_5$ are all hydrogen, deprotection of a compound of the general Formula V

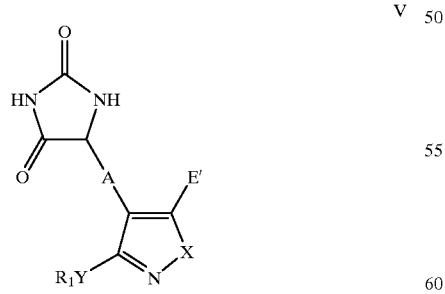

V wherein $R_1$, A, Y, X and E' are as previously defined;

c) in order to obtain a compound of Formula I wherein B is a group of Formula III, addition-elimination reaction of a compound of the general Formula VI with a compound of the general Formula VII:

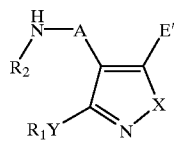

VI

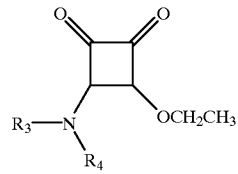

VII in which formulas $R_1$–$R_4$, A, X, Y and E' are previously defined;

d) In order to obtain a compound of Formula I, wherein B is a group of Formula III wherein $R^4$ and $R^2$ are linked to form a $C_{1-3}$ alkylene, $C_2$–$C_3$ alkenylene or $C_2$–$C_3$ alkynylene group optionally mono- or di-substituted with hydroxy or methyl, reacting a compound of Formula VIII

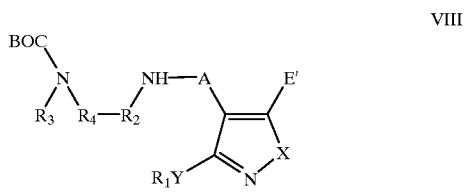

VIII wherein $R_1$, $R_3$, A, X, Y and E' are as previously defined; $R_4$ and $R_2$ are linked to form a group as defined above and BOC is t-butoxycarbonyl, with 3,4-diethoxy-3-cyclobuten-1,2-dion and subsequent ringclosure and deprotection;

e) in order to obtain a compound of Formula I wherein B is a group of Formula III and one or more of $R_2$–$R_4$ are different from hydrogen, alkylation of a compound of the general Formula IX

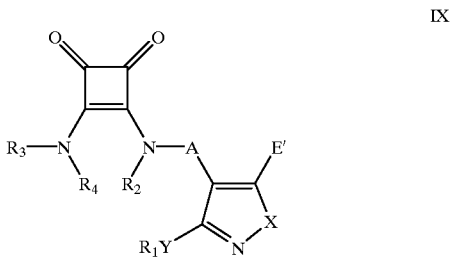

IX wherein $R_1$, $R_2$, $R_3$, $R_4$, A, X, Y and E' are as previously defined, at least one of $R_2$–$R_4$, however, being hydrogen;

f) in order to obtain a compound of Formula I or II, alkylating a compound having general Formula X

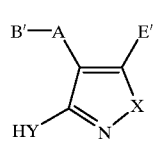

X wherein A, X, Y and E' are as previously defined and B' is as B except that in the definition of R$_b$, R$_c$ and R$_5$ hydrogen is replaced by a protection group, with an alkylating agent $R_1'Z$ wherein $R_1'$ is as $R_1$ except that it may not be hydrogen, thereby obtaining a mixture of the compounds XI and XII:

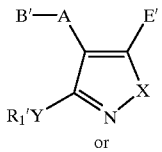

XI or

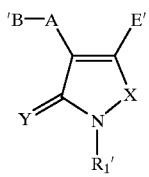

XII wherein A, X, Y, E' and B' are as defined above, and then separating and deprotecting the compounds;

g) in order to obtain a compound of Formula I wherein $R_5$ and/or $R_6$ is different from hydrogen, etsterification of a compound of formula XIII or XIV:

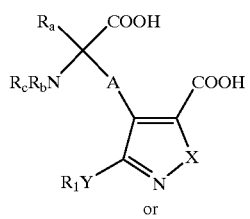

XIII or

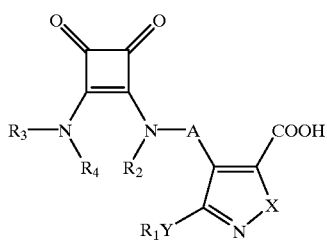

XIV wherein $R_1$, $R_2$, $R_3$, $R_4$, A, X, Y and $R_a$–$R_c$ are as previously defined;

h) in order to obtain a compound of Formula I wherein B is a —$CR_a(NR_bR_c)$—$COOR_5$ group wherein $R_a$, $R_b$, $R_c$ and $R_5$ are all hydrogen, and E is COOH in particular an enantiomeric pure compound, subjecting a compound of Formula XV

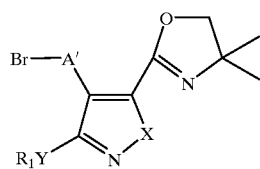

XV to a Schöllkopf Bis-Lactim Amino Acid synthesis and subsequent deprotection of the obtained bislactim ether having Formula XVI

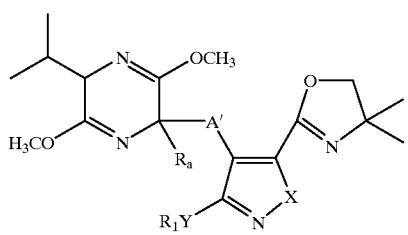

XVI in which formulas X, Y, $R_a$ and $R_1$ are as previously defined and A' is as defined for A except that it may not be a bond.

In the method of the invention preferred protection groups are as follows:

For E=COOH: 4,5-dihydro-4,4-dimethyloxazol-2-yl, $C_{1-6}$ alkyl or a benzyl group; for $R_5$=hydrogen: $C_{1-6}$ alkyl and $R_b$=hydrogen: $C_{1-6}$ alkylcarbonyl.

The one step deprotection according to method a) is carried out by treatment of the compound of Formula IV with a suitable aqueous acid, conveniently an 0.5–12 N aqueous solution of HCl, an aqueous solution of 48% HBr, or a saturated solution of HBr in acetic acid. The deprotection may also be carried out in successive steps by using aqueous acids and aqueous bases, conveniently successively in an aqueous acid such as 0.5–12 N HCl, an aqueous base such as 1–8 N NaOH and an aqueous acid such as 0.5–12 N HCl, or successively in an aqueous base such as 1–8 N NaOH and an aqueous acid such as 0.5–12 N HCl.

Starting materials of Formula IV are conveniently prepared from 3-alkoxy-4-methylisoxazole-5-carboxylic acid (WO95/12587, A1) by complete deprotection in an aqueous acid according to the above described deprotection conditions, optional esterification of the 3-hydroxy-4-methylisoxazole-5-carboxylic acid and subsequent alkylation with an appropriate halide or simply by alkylation. This is followed by bromination of the 4-methylisoxazole group and subsequent alkylation with an amino acid precursor e.g. diethyl acetamidomalonate. Other 4-alkylisoxazoles may be prepared by chain-elongation, e.g. alkylation with cyanide or diethyl malonate and subsequent transformation to the primary alkyl halide or aldehyde. The halide may be treated as outlined above. The aldehyde may be used as starting material fot the preparation of compounds of general formular V.

In b), the one step deprotection is carried out by treatment of a compound of Formula V with a suitable aqueous acid or aqueous base, conveniently in 0.5–8 N aqueous hydrochloric acid. The deprotection may also be performed in successive steps by using aqueous acids and aqueous bases as mentioned above for method a). The hydantoin ring may also be cleaved by the use of an aqueous solution of $Ba(OH)_2$, aqueous 10–70% sulphuric acid or by the use of enzymes such as hydantoinases. The cleavage of the hydantoin ring may be carried out either before or after the deprotection of the E-group. The $R_1$ group may have to be reintroduced by alkylation after complete deprotection of the hydantoin intermediate.

The hydantoin rings in the compounds of the general Formula V are conveniently formed according to the methods described by Ware, E.,*Chem.Rev.* 1950, 46, 403–470. The cleavage of the hydantoin ring is conveniently performed in analogy with the methods described by Curry, K. et al *J.Med.Chem.* 1988, 31, 864–867, Farrington, G. K. et al, *J.Med.Chem.* 1987, 30, 2062–2067, Grunewald, G. L. et al, *J.Med.Chem.* 1980, 23, 754–758, Hiroi, K. et al, *Chem.P-harm.Bull.* 1968, 16, 444–447 or Stark, G. R. et al, *J.Bi-ol.Chem.* 1963, 238, 214–226.

The starting material for preparation of compounds of Formula V may be obtained as outlined above for starting materials for method a). If A is a bond, the aldehyde may be prepared from the bromomethyl compound by bromination and subsequent transformation into the aldehyde.

The addition-elimination reaction according to method c) is conveniently performed in a protic organic solvent such as an alcohol, preferably in the presence of a suitable inorganic base such as aqueous NaOH at room temperature. The intermediates of Formula VII may be prepared by the methods described by Cohen, S. et al, *J.Amer.Chem.Soc.* 1966, 88, 1533–1536, EP-A2-0496561 or Kinney, W. A. et al, *J.Med.Chem.* 1992, 35, 4720–4726.

The intermediate of the general formula VI is readily obtained by a Gabriel synthesis of primary amines as described by Sheehan, J. C. et al., *J. Am. Chem. Soc.*, 1950, 72, 2786–88. The alkyl halide starting materials for this synthesis are conveniently obtained as described with respect to starting materials used in method a), cf. above.

The deprotection is conveniently performed by the use of an aqueous acid or an aqueous base, preferably 0.5–8 N HCl or aqueous 0.5–8 N NaOH, either at room temperature or at elevated temperatures.

In method d), the reaction and the subsequent ringclosure and deprotection are performed as described by Kinney et al., EP-A2-0496561.

The starting materials of formula VIII may be obtained by reacting e.g. 4-bromomethyl isoxazole obtained as described with respect to the starting materials in method a) with a mono-BOC-proteted alkylene diamine cf. EP-A2-0496561.

The alkylation of compounds of the general Formula IX according to method e) is conveniently performed in an inert organic solvent such as a suitable alcohol, ketone or dimethylformamide preferably in the presence of a suitable base such as sodium hydride, potassium carbonate or triethylamine, as described by Kinney, W. A., EP-A2-0496561. The starting materials of formula IX may be obtained by method c).

In method f), deprotection of compounds of general Formulas XI and XII is accomplished as described in method a) or by using a solution of hydrochloric acid in diethyl ether or another non-aqueous deprotection method. Starting material X is obtained as described with respect to the starting materials in method a) above.

In method g), the esterfication may be performed by methods well known in the art, e.g. treatment with an acidic solution of an alcohol. Starting materials are prepared in accordance with method a)–e) or h).

Resolution of the compounds of general formula I is conveniently performed by diastereomeric saltformation using optical active acids or bases, e.g. 1-phenylethylamine. In some cases, the resolution is conveniently performed by formation of diastereomeric compounds and subsequently separation of the diastereomers by flash chromatography or crystallisation. Certain diastereomers may conveniently be prepared by asymmetric synthesis by using Schöllkopf's Bis-Lactim Amino Acid synthesis, cf. method h). In this synthesis, starting materials are alkyl halides obtained as described above for starting materials for method a). The protecting group for the 5-carboxyisoxazole group is preferably an 2-oxazoline group prepared from the corresponding 5-cyanoisoxazole (WO95/12587, A1) by condensation with an aminoalcohol.

Salts of the compounds of the invention are easily prepared by methods well known in the art, i.e. by reacting the compound with either the equivalent amount of acid or base in an aqueous miscible solvent, such as acetone or ethanol, with isolation of the salt by concentration and cooling, or reacted with an excess of the acid or base in an aqueous immiscible solvent such as ethyl ether or chloroform, with the desired salt separating directly. These salts may also be prepared by the classical method of double decomposition of appropriate salts.

The compounds of general Formula I and the pharmaceutically acceptable acid addition salts thereof may be administered in any suitable way, e.g. orally or parenterally, and the compounds may be presented in any suitable form for such administration, e.g. in the form of tablets, capsules, powders, syrups or solutions or dispersions for injection.

An effective daily dose of a compound of general Formula I or a pharmaceutically acceptable salt thereof is from 10 µg/kg to 50 mg/kg body weight.

EXAMPLES

In the following the invention is further illustrated by way of examples which may in no way be construed as limiting for the invention.

All melting points were determined on a Büchi SMP-20 apparatus and are uncorrected. $^1$H NMR and $^{13}$C NMR spectra were recorded on a Brucker 250 MHz spectrometer (250.13 MHz for $^1$H NMR and 62.90 MHz for $^{13}$C NMR) using TMS as an internal standard if not otherwise stated.

Mass spectra were obtained on a Quattro MS-MS system from VG Biotech, Fisons Instruments connected to an HP 1050 modular HPLC system. 20–50 µl of sample (10 µg/ml) dissolved in a mixture of 1% acetic acid in acetonitrile/water=1:1 or in a mixture of acetonitril/water/aqueous ammonia (25%)=25:25:1 (zwitterions) was introduced via the autosampler at a flow of 30 µl/min into the Electrospray Source. Spectra were recorded at standard conditions to obtain molecular weight information ((M+H)$^+$) or ((M–H)). The background was subtracted.

Analytical HPLC was carried out on a 150×4.6 mm Lichrocart 250–4 (Merck) column eluted at 35° C. with 1 mL/min of methanol/0.01 M ammonium acetate, pH 8=3:2. The instrumentation used consisted of a L6200 HPLC pump, a L5025 column thermostat and a L4000A UV-VIS detector (set at 230 nm). Diastereomeric purities expressed as diastereomeric excess (de) were calculated from peak areas.

Chiral HPLC analysis was performed on a 150×4.6 mm Sumichiral OA-5000 column eluted at ambient temperature with 1 mL/min of 5 mM $CuSO_4$ (aq). The instrumentation used consisted of an AS 2000 autosampler, a L6200 HPLC pump, a T6300 column thermostat, a L4250 UV-VIS detector (set at 240 nm), and a D 6000 computer interface, all from Merck-Hitachi. Enantiomeric purities expressed as enantiomeric excess (ee) were calculated from peak areas.

Example 1

(RS)-2-Amino-3-(5-carboxy-3-methoxyisoxazol-4-yl)propionic Acid Hydrate (Comp. 1)

1) 3-Hydroxy-4-methylisoxazole-5-carboxylic Acid

3-Ethoxy-4-methylisoxazole-5-carboxylic acid (15 g, 88 mmol) and 47% HBr (aq) (150 mL) was boiled under reflux for 6 h. The solution was cooled and crystalline title compound was collected by filtration (8.7 g, 69%): mp 257–259° C. The acidic filtrate was added water (100 mL), and extracted with diethyl ether (6×400 mL). The organic extracts were washed with brine (100 mL), dried ($MgSO_4$)

and concentrated in vacuo to give crude title compound (3.0 g, 24%). Overall yield of 93%. A mixture of the two crops were used in the next step.

2) Ethyl 3-Hydroxy-4-methylisoxazole-5-carboxylate

3-Hydroxy-4-methylisoxazole-5-carboxylic acid (6.0 g, 42 mmol) and a saturated solution of HCl in EtOH (110 mL) was boiled under reflux for 4 h. The solution was concentrated in vacuo and the residue dissolved in EtOAc, dried (MgSO$_4$) and evaporated in vacuo to give crude title compound (7.2 g, 100%). A small sample was recrystallized (EtOAc/heptane) to give colorless crystals: mp 133–134° C. The crude product was used in the next step without further purification.

3) Ethyl 3-Methoxy-4-methylisoxazole-5-carboxylate

A mixture of ethyl 3-hydroxy-4-methylisoxazole-5-carboxylate (1.0 g, 5.8 mmol), methyl iodide (0.4 mL, 5.8 mmol) and K$_2$CO$_3$ (1.6 g, 11.7 mmol) in DMF (40 mL) was heated at 40° C. for 1 h. The mixture was poured onto an ice/water mixture (100 mL) and extracted with diethyl ether (3×100 mL). The organic extracts were washed with water (2×50 mL), brine (50 mL), dried (MgSO$_4$) and concentrated in vacuo (0.8 g, 74%). The procedure was repeated in order to obtain crude product equivalent to 17.5 mmol of starting material which was subjected to flash chromatography (silica gel, eluent: dichloromethane/diethyl ether=9:1) affording crude title compound as a yellow oil (1.4 g, 43%) which was used in the next step without further purification.

4) Ethyl 4-(Bromomethyl)-3-methoxyisoxazole-5-carboxylate

Ethyl 3-Methoxy-4-methylisoxazole-5-carboxylate (1.3 g, 7.0 mmol), NBS (1.4 g, 7.9 mmol), dibenzoyl peroxide (catalytic amount) and tetrachloromethane (40 mL) was boiled under reflux for 10 h. The mixture was cooled, filtered and concentrated in vacuo to give crude title compound as a yellow oil (1.8 g, 97%). The crude product was used in the next step without further purification.

Ethyl 2-Acetamido-2-(ethoxycarbonyl)-3-[5-(ethoxycarbonyl)-3-methoxyisoxazol-4-yl]proionate A mixture of diethyl acetamidomalonate (1.6 g, 7.4 mmol) and potassium tert-butoxide (0.9 g, 8.0 mmol) in N-methylpyrrolidone (30 mL) was stirred at room temperature for 30 min. Ethyl 4-(bromomethyl)-3-methoxyisoxazole-5-carboxylate (1.8 g, 6.8 mmol) in N-methylpyrrolidone (10 mL) was added (temp 22–28° C.) and the resulting mixture was stirred at room temperature for 1.5 h. The reaction mixture was poured onto an ice/water mixture (100 mL) and the aqueous phase was extracted with EtOAc (3×150 mL). The organic extracts were washed with an aqueous solution of potassium tert-butoxide, water (100 mL) and brine (100 mL), dried (MgSO$_4$) and concentrated in vacuo. Flash chromatography (silica gel, eluent: EtOAc/heptane=1:1) afforded crude title compound (1.8 g, 66%). A small sample was recrystallized (EtOAc/heptane) to give colourless crystals: mp 78–80° C. The crude product was used in the next step without further purification.

6) (RS)-2-Amino-3-(5-carboxy-3-methoxyisoxazol-4-yl)propionic Acid Hydrate (Comp. 1)

A suspension of ethyl 2-acetamido-2-(ethoxycarbonyl)-3-[5-(ethoxycarbonyl)-3-methoxyisoxazol-4-yl]propionate (1.2 g, 3.0 mmol) in 0.5 M HCl (100 mL) was boiled under reflux for 48 h. The mixture was cooled, washed with dichloromethane (100 mL) and diethyl ether (2×100 mL), filtered and concentrated in vacuo. Water was added (5 mL) and the pH adjusted to about 3 by addition of NaOH (0.1 M and 1 M). The aqueous phase was reduced in vacuo (2 mL) and a precipitate collected by filtration. The precipitate was stirred in water (2 mL) at room temperature for 24 h affording Comp. 1 after filtration (70 mg, 10%): mp 222–225° C. (dec); $^1$H NMR (DMSO-d$_6$) δ2.88 (dd, 1 H), 3.01 (dd, 1 H), 3.85–3.96 (m, 1 H), 3.90 (s, 3 H); $^{13}$C NMR (DMSO-d$_6$) d 22.70, 52.38, 57.32, 103.25, 159.43, 165.95, 170.66 (2 C); MS ((M+H)$^+$) m/z 231. Anal. (C$_8$H$_{10}$N$_2$O$_6$·0.25H$_2$O) calcd, C, 40.94; H, 4.51; N, 11.94; found, C, 41.01; H, 4.37; N, 11.91.

The following compounds were prepared in a similar way:

(RS)-2-Amino-3-(5-carboxy-3-ethoxyisoxazol-4-yl)propionic Acid (Comp. 2).

Mp 238–240° C. (dec); $^1$H NMR (DMSO-d$_6$) d 1.34 (t, 3 H), 2.90 (dd, 1 H), 3.03 (dd, 1 H), 3.96 (dd, 1 H), 4.23 (q, 2 H); $^{13}$C NMR (DMSO-d$_6$) δ14.46, 22.41, 51.89, 65.63, 103.34, 159.22, 164.97, 169.75, 170.40; MS ((M+H)$^+$) m/z 245. Anal. (C$_9$H$_{12}$N$_2$O$_6$) calcd, C, 44.27; H, 4.95; N, 11.47; found, C, 44.10; H, 4.92; N, 11.34.

(RS)-2-Amino-3-(5-carboxy-3-isopropoxyisoxazol-4-yl)propionic Acid (Comp. 3)

Mp 242–243° C. (dec); $^1$H NMR (DMSO-d$_6$) d 1.32 (dd, 6 H), 2.88 (dd, 1 H), 3.01 (dd, 1 H), 3.96 (dd, 1 H), 4.79 (h, 1 H); $^{13}$C NMR (DMSO-d$_6$) δ21.57, 21.77, 22.35, 51.82, 73.13, 103.56, 159.22, 164.91, 169.08, 170.36; MS ((M+H)$^+$) m/z 259. Anal. (C$_{10}$H$_{14}$N$_2$O$_6$) calcd, C, 46.51; H, 5.46; N, 10.85; found, C, 46.37; H, 5.46; N, 10.83.

(RS)-2-Amino-3-(5-carboxy-3-hydroxyisoxazol-4-yl)propionic Acid Hydrate (Comp. 4)

Mp 175–177° C.; $^1$H NMR (DMSO-d$_6$) δ3.00 (d, 2 H), 3.88 (t, 1 H); $^{13}$C NMR (DMSO-d$_6$) δ23.07, 52.07, 105.84, 159.41, 162.11, 169.89, 170.78; MS ((M+H)$^+$) m/z 217. Anal. (C$_7$H$_8$N$_2$O$_6$·0.25H$_2$O) calcd, C, 38.10; H, 3.88; N, 12.70; found, C, 37.72; H, 3.98; N, 12.52.

Example 2

(RS)-2-Amino-3-(5-carboxy-2,3-dihydro-2-methyl-3-oxoisoxazol-4-yl)propionic Acid Hydrate (Comp 5)

Ethyl 2,3-Dihydro-2,4-dimethyl-3-oxoisoxazole-5-carboxylate

A mixture of ethyl 3-hydroxy-4-methylisoxazole-5-carboxylate (2.0 g, 11.7 mmol) and K$_2$CO$_3$ (4.0 g, 29 mmol) in ethanol (50 mL) was heated at 40° C. for a total of 26 h. Methyl iodide (0.8 mL, 13 mmol) was added after 1 h and an additional 3 times during the next 25 h. The solution was filtered and reduced in vacuo (according to $^1$H NMR, a 1:1 mixture of the title compound and ethyl 3-methoxy-4-methylisoxazole-5-carboxylate was obtained). Flash chromatography (silica gel, eluent: dichloromethane/diethyl ether=9:1 then 1:1) gave ethyl 3-Methoxy-4-methylisoxazole-5-carboxylate as a yellow oil (0.40, 18%) and title compound (0.45 g, 21%). A small sample of the latter was recrystallized (EtOAc/heptane) to give colorless crystals: mp 64–65° C. Crude title compound was used in the next step without further purification.

(RS)-2-Amino-3-(5-carboxy-2,3-dihydro-2-methyl-3-oxoisoxazol-4-yl)propionic Acid Hydrate (Comp 5)

The title compound was obtained by processes analogeous to those of steps 2)–6) of Example 1 using the product of 1) above (70 mg, colourless crystals, 72%). Mp 211–212° C. (dec); $^1$H NMR (DMSO-d$_6$) δ2.87 (dd, 1 H), 2.97 (dd, 1 H), 3.43 (s, 3 H), 3.92 (dd, 1 H); $^{13}$C NMR (DMSO-d$_6$) δ23.10, 32.32, 51.79, 106.51, 158.59, 162.37, 166.64, 170.35; MS ((M+H)$^+$) m/z 231. Anal. (C$_8$H$_{10}$N$_2$O$_6$.0.25H$_2$O) calcd, C, 40.94; H, 4.51; N, 11.94; found, C, 40.93; H, 4.55; N, 11.71.

The following compound was prepared in a similar way:

(RS)-2-Amino-3-(5-carboxy-2-ethyl-2,3-dihydro-3-oxo-isoxazol-4-yl)propionic Acid Monohydrate (Comp. 6)

$^1$H NMR (D$_2$O, 1,4-dioxane d 3.70) δ1.28 (t, 3 H), 3.19 (d, 2 H), 4.01 (q, 2 H), 4.18 (t, 1 H); $^{13}$C NMR (D$_2$O, 1,4-dioxane δ67.40) δ12.87, 23.85, 42.31, 53.27, 110.57, 159.88, 162.65, 166.67, 172.55; MS ((M+H)$^+$) m/z 245. Anal. (C$_9$H$_{12}$N$_2$O$_6$.H$_2$O) calcd, C, 41.22; H, 5.38; N 10.68; found, C, 41.28; H, 4.74; N, 10.27.

Example 3

(S)-2-Amino-3-(5-carboxy-3-ethoxyisoxazol-4-yl)propionic Acid (Comp (S)-2)

(R)-2-Amino-3-(5-carboxy-3-ethoxyisoxazol-4-yl)propionic Acid (Comp (R)-2)

1) 5-(4,5-Dihydro-4,4-dimethyl-1,3-oxazol-2-yl)-3-ethoxy-4-methylisoxazole

3-Ethoxy-4-methylisoxazole-5-carbonitrile (2.6 g, 17.1 mmol), 5.4 M NaOMe in MeOH (0.6 mL, 3.4 mmol) and EtOH (80 mL) was stirred at room temperature for 30 min. Acetic acid (2.2 mL, 39.3 mmol) and 2-amino-2-methylpropan-1-ol (1.8 mL, 18.8 mmol) were added, and the resulting mixture was boiled under reflux for 20 h. The reaction mixture was cooled, added water (100 mL) and extracted with EtOAc (3×100 mL). The organic extracts were washed with 1 M NaOH (50 mL), brine, dried (MgSO$_4$) and evaporated in vacuo. The residue was dissolved in EtOH (60 mL), a solution of KOH (1.8 g, 32 mmol) in water (12 mL) was added, and the mixture was stirred at room temperature for 20 h. EtOH was removed in vacuo, water was added (80 mL) and the aqueous phase extracted with EtOAc (3×100 mL). The organic extracts were washed with brine, dried (MgSO$_4$) and evaporated in vacuo. Flash chromatography (silica gel, eluent: EtOAc/heptane/triethylamine=75:25:1) gave crude title compound as a yellow oil (2.0 g, 52%).

2) 4-(Bromomethyl)-5-(4,5-dihydro-4,4-dimethyl-1,3-oxazol-2-yl)-3-ethoxyisoxazole 5-(4,5-Dihydro-4,4-dimethyl-1,3-oxazol-2-yl)-3-ethoxy-4-methylisoxazole (2.0 g, 8.9 mmol), NBS (1.75 g, 9.8 mmol) and tetrachloromethane (150 mL) was boiled under reflux for 5 h. The mixture was cooled, filtered and concentrated in vacuo. Flash chromatography (silica gel, eluent: toluene/EtOAc/triethylamine=100:10:1) gave the title compound as a yellow oil (2.0 g, 74%).

3) (2S,5R)-2,5-Dihydro-2-{[5-(4,5-dihydro-4,4-dimethyl-1,3-oxazol-2-yl)-3-ethoxyisoxazol-4-yl]methyl}-5-isopropyl-3,6-dimethoxypyrazine and (2R,2R)-2,5-Dihydro-2-{[5-(4,5-dihydro-4,4-dimethyl-1,3-oxazol-2-yl)-3-ethoxyisoxazol-4-yl]methyl}-5-isopropyl-3,6-dimethoxypyrazine A 1.6 M solution of butyllithium in hexane (1.9 mL, 3.0 mmol) was added to a precooled (−78° C.) solution of (2R)-(−)-2,5-dihydro-2-isopropyl-3,6-dimethoxypyrazine (0.5 mL, 2.8 mmol) in anhydrous tetrahydrofuran (8 mL). Stirring was continued at −78° C. for 10 min, 4-(bromomethyl)-5-(4,5-dihydro-4,4-dimethyl-1,3-oxazol-2-yl)-3-ethoxyisoxazole (0.85 g, 2.8 mmol) dissolved in tetrahydrofuiran (5 mL) was added and the resulting mixture stirred at −78° C. for 4.5 h. The reaction mixture was allowed to warm to room temperature and concentrated in vacuo. The residue was dissolved in diethyl ether (40 mL) and poured onto an ice/water mixture (40 mL). The layers were separated and the aqueous phase extracted with diethyl ether (2×40 mL). The organic extracts were washed with brine, dried (MgSO$_4$) and concentrated in vacuo. Flash chromatography (silica gel, eluent: heptane/EtOAc=3:1) gave the (2S,5R)-title compound as a yellow oil (0.65 g, 57%): de=99.2% (retention time ca. 38 min). Further elution afforded crude (2R,5R)-title compound as a yellow oil (38 mg, 3%).

4) (2R,5S)-2,5-Dihydro-2-{[5-(4,5-dihydro-4,4-dimethyl-1,3-oxazol-2-yl)-3ethoxyisoxazol-4-yl]methyl}-5-isopropyl-3,6-dimethoxypyrazine and (2S,5S)-2,5-Dihydro-2-{[5-(4,5-dihydro-4,4-dimethyl-1,3-oxazol-2-yl)-3-ethoxyisoxazol-4-yl]methyl}-5-isopropyl-3,6-dimethoxypyrazine The title compounds were obtained by a procedure as described in step 3) above using (2S)-(+)-2,5-dihydro-2-isopropyl-3,6-dimethoxypyrazine as starting material. Flash chromatography (silica gel, eluent: heptane/EtOAc=3:1) to give (2R,5S)-title compound as a yellow oil (0.8 g, 54%): de >99.2% (retention time ca. 38 min). Further elution afforded crude (2S,5S)-title compound as a yellow oil (60 mg, 4%).

5) (S)-2-Amino-3-(5-carboxy-3-ethoxyisoxazol-4-yl)propionic Acid (Comp (S)-2)

A suspension of (2S,5R)-2,5-dihydro-2-{[5-(4,5-dihydro-4,4-dimethyl-1,3-oxazol-2-yl)3-ethoxyisoxazol-4-yl]methyl}-5-isopropyl-3,6-dimethoxypyrazine (0.6 g, 1.5 mmol) in 1 M trifluoroacetic acid (200 mL) was boiled under reflux for 5 h. The reaction mixture was concentrated in vacuo (2 mL), the residue dissolved in water (50 mL) and washed with EtOAc (3×50 mL). The aqueous phase was filtered, evaporated in vacuo to dryness and the residue treated with water (10 mL). The precipitate which formed was stirred at room temperature for 24 h, collected by filtration and recrystallized (water) to afford compound (S)-2 as colourless crystals (0.12 g, 33%): mp 259–261° C. (dec); ee >99% (retention time ca. 30 min); $^1$H NMR (DMSO-d$_6$) δ1.34 (t, 3 H), 2.90 (dd, 1 H), 3.03 (dd, H), 3.96 (dd, 1 H), 4.23 (q, 2 H); MS ((M+H)$^+$) m/z 245. Anal. (C$_9$H$_{12}$N$_2$O$_6$) calcd, C, 44.27; H, 4.95; N, 11.47; found, C, 44.45; H, 4.96; N, 11.46.

6) (R)-2-Amino-3-(5-carboxy-3-ethoxyisoxazol-4-yl)propionic Acid (Comp. (R)-2)

A stirred solution of (2R,5S)-2,5-dihydro-2-{[5-(4,5-dihydro-4,4-dimethyl-1,3-oxazol-2-yl)-3-ethoxyisoxazol-4- yl]methyl}-5-isopropyl-3,6-dimethoxypyrazine (0.6 g, 1.5 mmol) and MeOH (7 mL) was added 0.25 M HCl (74 mL, 7.4 mmol), and the resulting mixture stirred at room temperature for 2 h. pH was adjusted to about 7 by addition of aqueous ammonia (0.5 M) and the MeOH removed in vacuo. pH was adjusted to 8–9 by addition of aqueous ammonia (0.5 M) and the aqueous phase extracted with EtOAc (4×50 mL). The organic extracts were washed with brine, dried (MgSO$_4$) and concentrated in vacuo. The residue was suspended in 1 M HCl and the mixture boiled under reflux for 4.5 h. The reaction mixture was concentrated in vacuo (2 mL), the residue dissolved in water (50 mL) and washed with EtOAc (3×50 mL). The aqueous phase was filtered, evaporated in vacuo to dryness and the residue treated with water (10 mL). The precipitate which formed was stirred at room temperature for 2 h, collected by filtration and recrystallized (water) to afford compound (R)-2 as colorless crystals (0.13 g, 36%): mp 258–260° C. (dec); ee >99% (retention time ca. 50 min); $^1$H NMR (DMSO-d$_6$) δ1.34 (t, 3 H), 2.90 (dd, 1 H), 3.03 (dd, 1 H), 3.96 (dd. 1 H), 4.23 (q, 2 H); MS ((M+H)$^+$) m/z 245. Anal. (C$_9$H$_{12}$N$_2$O$_6$) calcd, C, 44.27; H, 4.95; N, 11.47; found, C, 44.56; H, 4.95; N, 11.53.

Example 4

(RS)-2-Amino-3-[3-ethoxy-5-(1H-1,2,4-triazol-3-yl) isoxazol-4-yl]propionic Acid Hydrate (Comp 7)

N-[(Dimethylamino)methylidene]-3-ethoxy-4-methylisoxazole-5-carboxamide

A solution of 3-ethoxy-4-methylisoxazole-5-carboxamide (3.5 g, 21 mmol) in N,N-dimethylformamide dimethyl acetal (15 mL) was stirred at 120° C. for 15 min. After being cooled, the title compound was collected as a colourless crystals (4.2 g, 91%).

3-(3-Ethoxy-4-methylisoxazol-5-yl)-1H-1,2,4-triazole

To a solution of hydrazine hydrate (0.6 mL, 12.4 mmol) in acetic acid (15 mL) was added N-(dimethylamino) methylidene 3-ethoxy-4-methylisoxazole-5-carboxamide (1.8 g, 8.0 mmol). The reaction mixture was stirred at 90° C. for 15 min and then left at room temperature to crystallize affording pure title compound (1.2 g, 77%): mp 194–196° C. Water was added (40 mL) and the aqueous phase was extracted with EtOAc (3×30 mL). The organic extracts were washed with brine, dried (MgSO$_4$) and concentrated in vacuo to give crude title compound (0.3 g, 20%). The two crops were combined.

3-(3-Ethoxy-4-methylisoxazol-5-yl)-1-trityl-1H-1,2,4-triazole 3-(3-Ethoxy-4-methylisoxazol-5-yl)-1H-1,2,4-triazole (1.1 g, 5.7 mmol), triethylamine (2.5 mL, 18 mmol) and DMF (20 mL) was added trityl chloride (1.6 g, 5.7 mmol) in DMF (5 mL). The mixture was stirred at room temperature for 5 h and poured onto an ice/water mixture (200 mL). The aqueous phase was extracted with diethyl ether (3×200 mL) and the organic extracts were washed with an aqueous solution of Na$_2$CO$_3$ (10%) (200 mL) and brine (200 mL). The solution was dried (Na$_2$SO$_4$) and concentrated in vacuo to give crude title compound (2.5 g). A small sample was crystallized (EtOAc) to give a single isomer as colourless crystals: mp 181–183° C. The crude product was used in the next step without further purification.

3-[4-(Bromomethyl)-3-ethoxyisoxazol-5-yl]-1-trityl-1H-1,2,4-triazole

A mixture of 3-(3-ethoxy-4-methylisoxazol-5-yl)-1-trityl-1H-1,2,4-triazole (2.4 g, 5.5 mmol) and NBS (1.1 g, 6.2 mmol) in tetrachloromethane (150 mL) was boiled under reflux for 3 h. The reaction mixture was cooled, filtered and concentrated in vacuo to give crude title compound (2.8 g). The crude product was used in the next step without further purification.

Ethyl 2-Acetamido-3-[3-ethoxy-5-(1-trityl-1H-1,2,4-triazol-3-yl)isoxazol-4-yl]-2-(ethoxycarbonyl) propionate A mixture of diethyl acetamidomalonate (1.3 g, 6.0 mmol) and potassium tert-butoxide (0.73 g, 6.5 mmol) in N-methylpyrrolidone (30 mL) was stirred at room temperature for 30 min. 3-[4-(Bromomethyl)-3-ethoxyisoxazol-5-yl]-1-trityl-1H-1,2,4-triazole (2.8 g, 5.4 mmol) in N-methylpyrrolidone (20 mL) was added (temp 22–28° C.) and the resulting mixture was stirred at room temperature for 2 h. The reaction mixture was poured onto an ice/water mixture (250 mL) and the aqueous phase was extracted with EtOAc (3×250 mL). The organic extracts were washed with an aqueous solution of potassium tert-butoxide and brine, dried (Na$_2$SO$_4$) and concentrated in vacuo. Flash chromatography (silica gel, eluent: EtOAc/heptane/triethylamine= 50:50:2) gave the title compound (2.2 g, 62%): mp 145–149° C.

(RS)-2-Amino-3-[3-ethoxy-5-(1H-1,2,4-triazol-3-yl) isoxazol-4-yl]propionic Acid Hydrate (Comp 7)

A suspension of ethyl 2-acetamido-3-[3-ethoxy-5-(1-trityl-1H-1,2,4-triazol-3-yl)isoxazol-4-yl]-2-(ethoxycarbonyl)propionate (1.5 g, 2.3 mmol) in 1 M HCl (150 mL) was boiled under reflux for 24 h. The solution was cooled, washed with diethyl ether (2×150 mL) and dichloromethane (150 mL), filtered and concentrated in vacuo. Water was added (5 mL) and the pH adjusted to about 3.5 by addition of NaOH (0.1 M and 1 M) affording Compound 7 by filtration (0.35 g, 56%): mp 225–227° C. (dec); $^1$H NMR (DMSO-d$_6$) δ1.38 (t, 3 H), 2.94 (dd, 1 H), 3.18 (dd, 1 H), 3.58 (dd, 1 H), 4.30 (q, 2 H), 8.64 (s, 1 H); $^{13}$C NMR (DMSO-d$_6$) δ14.52, 23.60, 53.30, 65.93, 104.25, 146.18, 150.87, 158.44, 169.47, 170.51; MS ((M+H)$^+$) m/z 268. Anal. (C$_{10}$H$_{13}$N$_5$O$_4$.0.25H$_2$O) calcd, C, 44.20; H, 5.01; N, 25.77; found, C, 44.42; H, 5.29; N, 25.52.

Example 5

(RS)-2-Amino-3-[3-ethoxy-5-(5-tetrazolyl)isoxazol-4-yl]propionic acid (Comp. 8)

Was prepared by a method analogeous to the method of Example 4 from ethyl 2-acetamido-3-[3-ethoxy-5-(tetrazol-5-yl)isoxazol-4-yl]-2-(ethoxycarbonyl)propionate.

Example 6

(RS)-2-Amino-3-(3-benzyloxy-5-carboxyisoxazol-4-yl)propionic Acid (Comp. 9)

(RS)-2-Amino-3-(5-carboxy-3-hydroxyisoxazol-4-yl) propionic acid (3.5 g, 11.8 mmol) and a solution of HCl in ethanol (50 mL) was boiled under reflux for 2.5 h and evaporated to dryness in vacuo to give ethyl (RS)-2-amino-3-(5-ethoxycarbonyl-3-hydroxyisoxazol-4-yl)propionate (4.15 g, 100%).

A mixture of di-tert-butyl dicarbonate (3.1 g, 14 mmol), triethylamine (3.8 g, 37 mmol) and 1,4-dioxane (15 mL) was added to a solution of ethyl (RS)-2-amino-3-(5-ethoxycarbonyl-3-hydroxyisoxazol-4-yl)propionate (4.15 g, 11.7 mmol) in a water/1,4-dioxane (1:1) (50 mL), and the resulting mixture was stirred at room temperature for 16 h. The 1,4-dioxane was evaporated in vacuo, and the aqueous phase was acidified with dilute aqueous HCl. The aqueous phase was extracted with ethyl acetate, and the organic extracts washed with water, brine, dried ($MgSO_4$) and concentrated in vacuo. Flash chromatography ($SiO_2$, eluent: heptane/ethyl acetate/acetic acid (1:1, 4%)) gave ethyl (RS)-2-tert-butoxycarbonylamino-3-(5-ethoxycarbonyl-3-hydroxyisoxazol-4-yl)propionate as an oil (4.1 g, 92%).

A mixture of ethyl (RS)-2-tert-butoxycarbonylamino-3-(5-ethoxycarbonyl-3-hydroxyisoxazol-4-yl)propionate (3.2 g, 8.6 mmol), $K_2CO_3$ (2.4 g, 17.2 mmol) in acetone (40 mL) was heated to reflux temperature. Benzyl bromide (2.2 g, 12.9 mmol) was added, and the mixture was boiled under reflux for 1.5 h. Concentrated in vacuo and subjected to flash chromatography ($SiO_2$, eluent: heptane/ethyl acetate (2:1)) to give ethyl (RS)-2-[(tert-butoxycarbonyl)amino]-3-[3-benzyloxy-5-(ethoxycarbonyl)isoxazol-4-yl]propionate (1.64 g, 41%) and ethyl (RS)-2-[(tert-butoxycarbonyl)amino]-3-(2-benzyl-5-ethoxycarbonyl-2,3-dihydro-3-oxoisoxazol-4-yl)propionate (0.7 g, 18%).

A mixture of ethyl (RS)-2-[(tert-butoxycarbonyl)amino]-3-[3-benzyloxy-5-(ethoxycarbonyl)isoxazol-4-yl]propionate (0.65 mg, 1.4 mmol) and 1 M NaOH (50 mL) was boiled under reflux for 16 h. The mixture was cooled (5° C.), acidified with dilute aqueous HCl, and concentrated in vacuo. The residue was recrystallized from water to give (RS)-2-amino-3-(3-benzyloxy-5-carboxyisoxazol-4-yl) propionic acid (0.1 g, 23%): mp 209–211° C. (dec); $^1$H NMR (DMSO-$d_6$) δ2.95 (dd, 1 H), 3.05 (dd, 1 H), 3.99 (t, 1 H), 5.26 (s, 2 H), 7.31–7.52 (m, 5 H); MS ((M+H)$^+$) m/z 307. Anal. calcd, C, 54.89; H, 4.62; N, 9.15; found, C, 54.31; H, 4.56; N, 8.97.

The following compounds were prepared in a similar manner:

(RS)-2-Amino-3-(3-propoxy-5-carboxyisoxazol-4-yl)propionic Acid (Comp. 10)

Mp. 250–251° C. (dec). $^1$H NMR ($D_2O$, dioxane,1 M NaOD) d 0.95 (t, 3 H), 1.76 (se, 2 H), 2.78 (dd, 1 H), 2.90 (dd, 1 H), 3.42 (dd, 1 H), 4.17 (t, 2 H). $^{13}$C NMR d 12.3, 24.4, 29.8, 58.3, 74.9, 111.5, 164.3, 166.6, 173.9, 184.8. MS ((M+H)$^+$) m/z 259. Anal. calcd, C, 46.51; H, 5.46; N, 10.85; found C, 46.43; H, 5.41; N, 10.54.

(RS)-2-Amino-3-(3-butoxy-5-carboxisoxazol-4-yl)propionic Acid (Comp. 11)

Mp 238–240° C. (dec). $^1$H NMR ($D_2O$, dioxane, 1 M NaOD) d 0.95 (t, 3 H), 1.43 (se, 2 H), 1.76 (qui, 2 H), 2.8 (dd, 1 H), 2.91 (dd, 1 H), 3.44 (dd, 1 H), 4.25 (t, 2 H). $^{13}$C NMR NMR ($D_2O$, dioxan, 1 M NaOD) d 13.79, 19.30, 27.90, 31.03, 56.39, 71.27, 109.65, 162.39, 164.72, 172.02, 182.92. MS ((M+H)$^+$) m/z 273. Anal. calcd. C, 48.53; H, 5.92; N, 10.29; found, C, 48.80; H, 5.99; N, 10.34.

(RS)-2-Amino-3-(3-allyloxy-5-carboxyisoxazol-4-yl)propionic Acid (Comp. 12)

Mp 239–240° C. (dec). $^1$H NMR (DMSO-$d_6$) d 2.93 (dd, 1 H), 3.06 (dd, 1 H), 3.99 (dd, 1 H), 4.73 (d, 2 H), 5.29 (dd, 1 H), 5.44 (dd, 1 H), 6.05 (dq, 1 H).

Furtermore the following compounds are prepared similarly:
(RS)-2Amino-3-[3-(trans-2-but-ene-oxy)-5carboxyisoxazol-4-yl]propionic Acid
(RS)-2Amino-3-[3-(methyl-2-but-ene-oxy)-5carboxyisoxazol-4-yl]propionic Acid

Example 7

(RS)-2-Amino-3-(2-benzyl-5-carboxy-2,3-dihydro-3oxisoxazol-4-yl)propionic Acid, Hydrochloride, Monohydrate (Comp. 13)

A mixture of ethyl (RS)-2-[(tert-butoxycarbonyl)amino]-3-(2-benzyl-5-ethoxycarbonyl-2,3-dihydro-3-oxoisoxazol-4-yl)propionate (0.9 g, 1.9 mmol) and 1 M HCl was boiled under reflux for 5 h. The mixture was evaporated in vacuo to dryness (0.56 g, 80%): mp 146–148° C. (dec); $^1$H NMR (DMSO-$d_6$) δ3.08 (dd, 1 H), 3.19 (dd, 1 H), 4.17 (br s, 1 H), 5.16 (s, 2 H), 7.24–7.45 (m, 5 H); MS ((M+H)$^+$) m/z 307. Anal. calcd, C, 46.60; H, 4.76; N, 7.77; found, C, 46.88; H, 4.81; N, 7.96.

Example 8

Benzyl (RS)-2-Amino-3-(5-benzyloxycarbonyl-3-ethoxyisoxazol-4-yl)propionate Hydrochloride (Comp. 14)

A mixture of di-tert-butyl dicarbonate (1.1 g, 4.9 mmol), $NaHCO_3$ (1.1 g, 13 mmol) and 1,4-dioxane (3 mL) was added to a solution of (RS)-2-amino-3-(5-carboxy-3-ethoxyisoxazol-4-yl)propionic acid (1.0 g, 4.1 mmol) in a water/1,4-dioxane (1:1) (10 mL), and the resulting mixture was stirred at room temperature for 16 h. The 1,4-dioxane was evaporated in vacuo, and the aqueous phase was acidified with dilute aqueous HCl. The aqueous phase was extracted with ethyl acetate, and the organic extracts washed with water and brine. Dried ($MgSO_4$), concentrated in vacuo and subjected to flash chromatography ($SiO_2$, eluent:, ethyl acetate/ethanol/acetic acid (3:1, 4%)) to give (RS)-2-[(tert-butoxycarbonyl)amino]-3-(5-carboxy-3-ethoxyisoxazol-4-yl)propionic acid (1.4 g, 100%)

A mixture of (RS)-2-[(tert-butoxycarbonyl)amino]-3-(5-carboxy-3-ethoxyisoxazol-4yl)propionic acid (1.4 g, 4.1 mmol), benzyl bromide (1.4 g, 8.2 mmol) in benzene/tetrahydrofuran (4:1) was added 1,8-diazabicyclo[5.4.0]undec-7-ene (1.3 g, 8.6 mmol) and the resulting mixture was boiled under reflux for 3 h. The mixture was filtered and evaporated in vacuo. Flash chromatography ($SiO_2$, eluent:, ethyl acetate/heptane (1:3)) gave benzyl (RS)-2-[(tert-butoxycarbonyl)amino]-3-(5-benzyloxycarbonyl-3-ethoxyisoxazol-4-yl)propionate as an oil (1.9 g, 86%).

A mixture of benzyl (RS)-2-[(tert-butoxycarbonyl)amino]-3-(5-benzyloxycarbonyl-3-ethoxyisoxazol-4-yl)propionate (1.9 g, 3.6 mmol) and a saturated solution of HCl in dietyl ether (40 mL) was boiled under reflux for 2 h. The formed crystals were collected by filtration, stirred with ethyl acetate, and collected by filtration (0.53 g, 32%): mp 142–144° C.; $^1$H NMR (DMSO-$d_6$) δ1.32 (t, 3 H), 3.17 (dd, 1 H), 3.25 (dd, 1 H), 4.17–4.32 (m, 3 H), 5.09 (dd, 2 H), 5.39 (s, 2 H), 7.24–7.53 (m, 10 H); MS ((M+H)$^+$) m/z 425. Anal. calcd, C, 59.93; H, 5.48; N, 6.08; found, C, 59.70; H, 5.49; N, 6.26.

Example 9

Ethyl (RS)-2-Amino-3-(3-ethoxy-5-ethoxycarbonylisoxazol-4-yl)propionate, Oxalate (Comp. 15)

A mixture of (RS)-2-amino-3-(5-carboxy-3-ethoxyisoxazol-4-yl)propionic acid (2.0 g, 8.2 mmol) and a solution of HCl in ethanol (35 mL) was boiled under reflux for 3 h to give ethyl (RS)-2-amino-3-(5-carboxy-3-ethoxyisoxazol-4-yl)propionate. Ethyl (RS)-2-Amino-3-(5-carboxy-3-ethoxyisoxazol-4-yl)propionate (0.6 g) was added a dilute solution of NaOH, and the aqueous phase was extracted with ethyl acetate. The organic extracts were washed with brine, dried (MgSO$_4$), filtered and evaporated to dryness in vacuo. The residue was dissolved in acetone (6 mL) and added a solution of oxalic acid (0.14 g, 1.6 mmol) in acetone (6 mL), and the formed precipitate was collected by filtration (110 mg, 10%): mp 159–161° C.; $^1$H NMR (DMSO-d$_6$) δ1.11 (t, 3 H), 1.32 (t, 3 H), 1.36 (t, 3 H), 3.02 (dd, 1 H), 3.11 (dd, 1 H), 3.98–4.16 (m, 3 H) 4.32 (q, 2 H), 4.37 (q, 2 H); MS ((M+H)$^+$) m/z 301. Anal. calcd, C, 46.15; H, 5.69; N, 7.18; found, C, 46.38; H, 5.69; N, 7.36.

Example 10

Butyl (RS)-2-amino-3-(5-butoxycarbonyl-3-ethoxyisoxazol-4-yl)propionate, oxalate (Comp. 16)

The compound was obtained in a similar manner as described in Example 9 by using a solution of HCl in butanol. mp 120–121° C.; $^1$H NMR (DMSO-d$_6$) δ0.84 (t, 3 H), 0.92 (t, 3 H), 1.14–1.31 (m, 2 H), 1.31–1.51 (m, 4 H), 1.37 (t, 3 H) 1.62–1.75 (m, 2 H), 3.01 (dd, 1 H), 3.13 (dd, 1 H), 3.98–4.09 (m, 3 H), 4.16-4-436 (m, 4 H); MS ((M+H)$^+$) m/z 357. Anal. calcd, C, 51.11; H, 6.79; N, 6.28; found, C, 51.06; H, 6.82; N, 6.35.

Example 11

[4-(2-Amino-3,4-dioxocyclobut-1-en-1-yl) aminomethyl]-3-ethoxyisoxazole-5-carboxylic Acid (Comp. 17)

Ethyl 3-Ethoxy-4-methylisoxazole-5-carboxylate

Acetyl chloride (25 mL, 0.35 mol) was added to EtOH (250 mL) at 0° C. and the solution was stirred at 0° C. for 20 min. A solution of 3-ethoxy-4-methylisoxazole-5-carboxylic acid (WO95/12587,A1) (18 g, 0.10 mol) in EtOH (20 ml) was added and the resulting mixture was boiled under reflux for 4 h. The mixture was cooled, added NaHCO$_3$ (200 mL) and extracted with diethylether (3×300 mL). The organic extracts were dried (MgSO$_4$) and concentrated in vacuo to afford crude title compound (18 g, 86%).

Ethyl 4-Bromomethyl-3-ethoxyisoxazole-5-carboxylate

Ethyl 3-Ethoxy-4-methylisoxazole-5-carboxylate (18 g, 91 mmol), NBS (17.5 g, 100 mmol), dibenzoyl peroxide (1 g, 4.1 mmol) in tetrachloromethane (500 mL) was boiled under reflux for 16 h. The mixture was cooled, filtered and concentrated in vacuo to afford the crude title compound (24.5 g, 97%).

Ethyl 3-Ethoxy-4-phthalimidomethylisoxazole-5-carboxylate

A solusion of ethyl 4-bromomethyl-3-ethoxyisoxazole-5-carboxylate (5 g, 17.9 mmol) in DMF (85 mL) was added to a suspension of potassium phthalimid (3.6 g, 19,7 mmol) in DMF (125 mL) at 90° C. The resulting mixture was stirred at 90° C. for 40 min, then cooled and concentrated in vacuo. Water (250 mL) was added and the aqueous phase was extracted with diethylether (2×200 mL). The organic extracts were dried (MgSO$_4$) and concentrated in vacuo to give a crude product which was recrystallized (EtOH) to yield the title compound (3.70 g, 60%): mp 93–94° C.

4-Aminomethyl-3-ethoxyisoxazole-5-carboxylic Acid Hydrochloride

A solution of ethyl 3-ethoxy-4-phthalimidomethylisoxazole-5-carboxylate in 1 M NaOH was boiled under reflux for 45 min. The mixture was cooled, added concd HCl and extracted with diethylether (3×400 ml). The organic extracts were concentrated in vacuo, added 1 M HCl (600 mL) and boiled under reflux for 1 h. After cooling the mixture was washed with diethylether (3×600 mL) and concentrated in vacuo to give a crude product which was recrystallized (acetic acid) to yield the title compound (1.5 g, 82%): mp 215–216° C. (dec).

[4-(2-Amino-3,4-dioxocyclobut-1-en-1-yl) aminomethyl]-3-ethoxyisoxazole-5-carboxylic Acid To a solution of 4-aminomethyl-3-ethoxyisoxazole-5-carboxylic acid hydrochloride (1.2 g, 5.4 mmol) and 3-amino-4-ethoxy-cyclobut-3-en-1,2-dione (0.60 g, 5.9 mmol) in EtOH (300 ML) was added 1 M NaOH (12 mL). The resulting suspension was stirred at room temperature for 16 h, then concentrated in vacuo, added water (100 mL) and washed with EtOAc (2×100 mL). The pH was adjusted to ca. 3 by addition of 1 M HCl. The precipitate was filtered off and recrystallized (water) to afford the title compound as a yellow powder (0.71 g, 47%): mp 236–238° C. (dec). $^1$H NMR (DMSO-d$_6$) d 1.30 (t, 3 H), 4.22 (q, 2 H), 4.68 (bs, 2 H). $^{13}$C NMR (DMSO-d$_6$) δ14.41, 35.27, 65.54, 107.16, 159.14, 163.54, 168.71, 169.15, 169.73, 183.20, 183.34. MS ((M+H)$^+$) m/z 282. Anal. (C$_{11}$H$_{11}$N$_3$O$_6$, 2.25 H$_2$O) calcd, C, 41.06; H, 4.86; N, 13.06; found, C, 41.16; H, 4.46; N, 12.96.

Pharmacology

The compounds of the invention were tested in accordance with the following well recognised and reliable test methods.

[$^3$H]AMPA Binding

In this test the affinity of a drug for AMPA receptors is determined by measuring the ability to displace [$^3$H]AMPA from AMPA receptors.

The test was carried out in accordance with a modified version of the method of Honoré, T. and Nielsen, M., Neurosci.Lett. 1985, 54, 27–32. The test was carried out in the presence of KSCN. This means that only the [$^3$H]AMPA high affinity binding sites were labelled.

The membrane preparations used were obtained in accordance with the method of Ransom, R. W. and Stec, J. Neurochem. 1988, 51, 830–836.

The Cortical Wedge Model

The Cortical wedge model is a test in which slices of rat brain is examined in vitro in order to quantify the effect of ligands at the various Glu-receptors and evaluate the pharmacological profile of the ligands (i.e. agonist/antagonist properties). The test was performed as described by Harrison, N. L. and Simmonds, M. A. Br.J.Pharmacol. 1985, 84, 381–391 as modified according to Wheatley, P. L. Br.J.Pharmacol. 1986, 87, 159P.

TABLE 1

| Compound | Profile | Cortical Wedge EC$_{50}$ (μM) | pK$_i$ | Receptor subtype |
|---|---|---|---|---|
| 1 | Agonist | 1.2 | | AMPA |
| 2 | Agonist | 4.8 | | AMPA |
| (S)-2 | Agonist | 4.4 | | AMPA |
| (R)-2 | Antagonist | | 3.28 | AMPA |
| 3 | Agonist | 40.0 | | AMPA |
| 8 | Agonist | 2000 | | AMPA |
| 10 | Agonist | 80 | | AMPA |
| 11 | Part. Agonist | 325 | | AMPA |
| 12 | Agonist | 40 | | AMPA |
| 13 | Antagonist | | 3.5 | NMDA |
| 17 | Antagonist | | 3.3 | NMDA |

Result

The compounds were found to be excitatory amino acid (EAA) receptor ligands. Some of the compounds were found to be agonists at the AMPA receptors and other compounds were found to be selective AMPA or NMDA receptor antagonists. The compounds showed activity in the μM range.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, lactose, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the vehicle, preferably sterile water, adjusting the solution to the desired volume, sterilisation of the solution and filling in suitable ampules or vials. Any suitable additive conventionally used in the art may be added, such as tonicity agents, preservatives, antioxidants, etc.

What is claimed is:

1. A (3-alkoxyisoxazol-4-yl)-substituted 2-amino carboxylic acid derivative having general Formula I or II

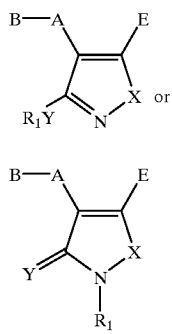

wherein $R_1$ is hydrogen, $C_{1-6}$ alkyl, $C_{2-6}$ alkenyl, $C_{2-6}$ alkynyl, cycloalk(en)yl, cycloalk(en)yl-$C_{1-6}$alk(en/yn)yl or phenyl-$C_{1-6}$alk(en/yn)yl, the phenyl group being optionally substituted with $CF_3$, halogen, $C_{1-6}$ alkyl or $C_{1-6}$ alkoxy;

A is a bond or a spacer group selected from $C_{1-6}$ alkylene, $C_{2-6}$ alkenylene, $C_{2-6}$ alkynylene, and cycloalkylene;

B is a group —$CR_a$ (NR$_b$R$_c$)—COOR$_5$ wherein $R_a$–$R_c$ are independently hydrogen or $C_{1-6}$ alkyl, and $R_5$ is defined as $R_1$ or pivaloyloxymethyl, or B is a group of Formula III

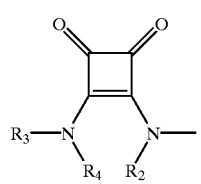

wherein $R_2$, $R_3$ and $R_4$ are independently selected from the group consisting of a) hydrogen, $C_{1-6}$ alkyl, $C_{2-6}$ alkenyl, $C_{2-6}$ alkynyl, cycloalk(en)yl, cycloalk(en)yl-$C_{1-6}$ alk(en/yn)yl, phenyl-$C_{1-6}$ alkyl, thienyl-$C_{1-6}$-alkyl, and b) $C_{1-6}$ alkyl, $C_{2-6}$ alkenyl and $C_{2-6}$ alkynyl in which one or more carbon atoms are replaced by N, O, and/or S, or $R_3$ and $R_4$ are connected, thereby forming a $C_2$–$C_6$ alkylene, $C_2$–$C_6$ alkenylene or $C_2$–$C_6$ alkynylene group, or $R_4$ and $R_2$ are connected in order to form a $C_1$–$C_3$ alkylene, $C_2$–$C_3$ alkenylene or $C_2$–$C_3$ alkynylene group optionally mono- or di-substituted with hydroxy or methyl, or to form $CH_2$—O—$CH_2$;

E is $COOR_6$, where $R_6$ is defined as $R_5$;

X is O; Y is O or S; or a pharmaceutically acceptable salt thereof.

2. A compound of claim 1 which has Formula I.
3. A compound of claim 1 which has Formula II.
4. A compound of claim 1, wherein $R_6$ is not hydrogen.
5. A compound of claim 1, wherein E is COOH.
6. A compound of claim 1, wherein B is a group of the formula $CR_a(NR_bR_c)$—$COOR_5$.
7. A compound of claim 6, wherein $R_b$ and $R_c$ are hydrogen and $R_a$ is hydrogen or $C_{1-6}$ alkyl.
8. A compound of claim 1, wherein $R_5$ is hydrogen.
9. A compound of claim 1, wherein $R_5$ is not hydrogen.
10. A compound of claim 1, wherein B is a group of the formula III.
11. A compound of claim 10, wherein $R_2$, $R_3$ and $R_4$ are hydrogen or $C_{1-6}$ alkyl, or $R_4$ and $R_2$ are connected in order to form a $C_1$–$C_3$ alkylene group.
12. A compound of claim 11, wherein each of $R_2$, $R_3$ and $R_4$ are hydrogen.
13. A compound of claim 1, wherein Y is oxygen.
14. A compound of claim 1, wherein Y is sulfur.
15. A compound of claim 1, wherein $R_1$ is $C_{1-6}$ alkyl, $C_{2-6}$ alkenyl or $C_{2-6}$ alkynyl.
16. A compound of claim 1, wherein A is a bond or $C_1$–$C_3$ alkylene.
17. A compound of claim 2, wherein A is a bond or $C_1$–$C_3$ alkylene, B is —$CH(NH_2)$—COOH or a group of Formula III wherein each of $R_3$, $R_4$ and $R_2$ are hydrogen, Y is oxygen, and $R_1$ is $C_{1-6}$ alkyl, $C_{2-6}$ alkenyl or $C_{2-6}$ alkynyl.
18. A compound of claim 1 wherein $R_6$ is selected from the group consisting of $C_{1-6}$ alkyl phenyl-$C_{1-6}$, alk(en/yn)yl and pivaloyloxymethyl.
19. A compound of claim 15 wherein $R_1$ is selected from the group consisting of methyl, ethyl, propyl or propargyl.
20. A compound of claim 16 wherein said $C_{1-3}$ alkylene is methylene.
21. A compound of claim 17 wherein $R_1$ is selected from the group consisting of methyl, ethyl, propyl or propargyl.
22. A pharmaceutical composition comprising a compound of claim 1 together with a pharmaceutically acceptable carrier or diluent.
23. A method of treating cerebral ischaemia, Huntington's disease, epileptic disorders, Parkinson's disease, Alzheimer's disease, schizophrenia, pain, depression or anxiety, said method comprising administering a therapeutically effective amount of a compound of claim 1 to a patient in need thereof.

* * * * *